United States Patent [19]

Maehama et al.

[11] Patent Number: 5,048,070
[45] Date of Patent: Sep. 10, 1991

[54] X-RAY TUBE SUPPORT APPARATUS

[75] Inventors: Tomio Maehama; Kiyoaki Inoue, both of Ootawara, Japan

[73] Assignee: Kabushiki Kaisha Toshiba, Kawasaki, Japan

[21] Appl. No.: 448,914

[22] Filed: Dec. 12, 1989

[30] Foreign Application Priority Data

Dec. 13, 1988 [JP] Japan ................................. 63-314295

[51] Int. Cl.$^5$ ......................... H05G 1/02; H05G 1/64
[52] U.S. Cl. .................................... 378/197; 378/193; 378/198; 378/205; 378/10; 378/94
[58] Field of Search ............... 378/193, 195, 196, 197, 378/198, 205, 94, 10, 12, 170, 177

[56] References Cited

U.S. PATENT DOCUMENTS

| 3,121,793 | 2/1964 | Thomas | 378/197 |
| 3,891,856 | 6/1975 | Amor, Jr. et al. | 378/197 |
| 4,024,403 | 5/1977 | Bernstein et al. | 378/197 |
| 4,356,400 | 10/1982 | Polizzi et al. | 378/205 |
| 4,435,830 | 3/1984 | Suzuki et al. | 378/197 |
| 4,501,011 | 2/1985 | Hauck et al. | 378/196 |

FOREIGN PATENT DOCUMENTS

| 3423001 | 1/1986 | Fed. Rep. of Germany . |
| 2026206 | 1/1980 | United Kingdom . |
| 8810095 | 12/1988 | World Int. Prop. O. . |

Primary Examiner—Edward P. Westin
Assistant Examiner—Don Wong
Attorney, Agent, or Firm—Oblon, Spivak, McClelland, Maier & Neustadt

[57] ABSTRACT

An X-ray tube support apparatus includes: an X-ray tube support mechanism for supporting an X-ray tube to be vertically extendible/movable; a guide unit, having moving paths which allow movement in two-dimensional directions parallel to a ceiling surface, for supporting the X-ray tube support mechanism, and guiding the X-ray tube to a central position of one photographing table; a plurality of position sensors, arranged in a vertical moving path of the X-ray tube support mechanism, and two-dimensional moving paths to the central position of the photographing table, for detecting vertical and two-dimensional moving positions of the X-ray tube support mechanism; a plurality of fixing units, arranged in the two-dimensional moving paths of the guide unit and the vertical moving path of the X-ray tube support mechanism, for fixing the X-ray tube support mechanism at each moving position; and a determination unit for storing position data in accordance with the central position of the photographing table and a set distance from a focal point of the X-ray tube to an X-ray photographing system, comparing the position data with a position detection signal of the position detected by each position sensor, and outputting a lock instruction to the corresponding one of the fixing units when it is determined that the position data coincides with the position detection signal, thus locking the X-ray tube support mechanism.

11 Claims, 5 Drawing Sheets

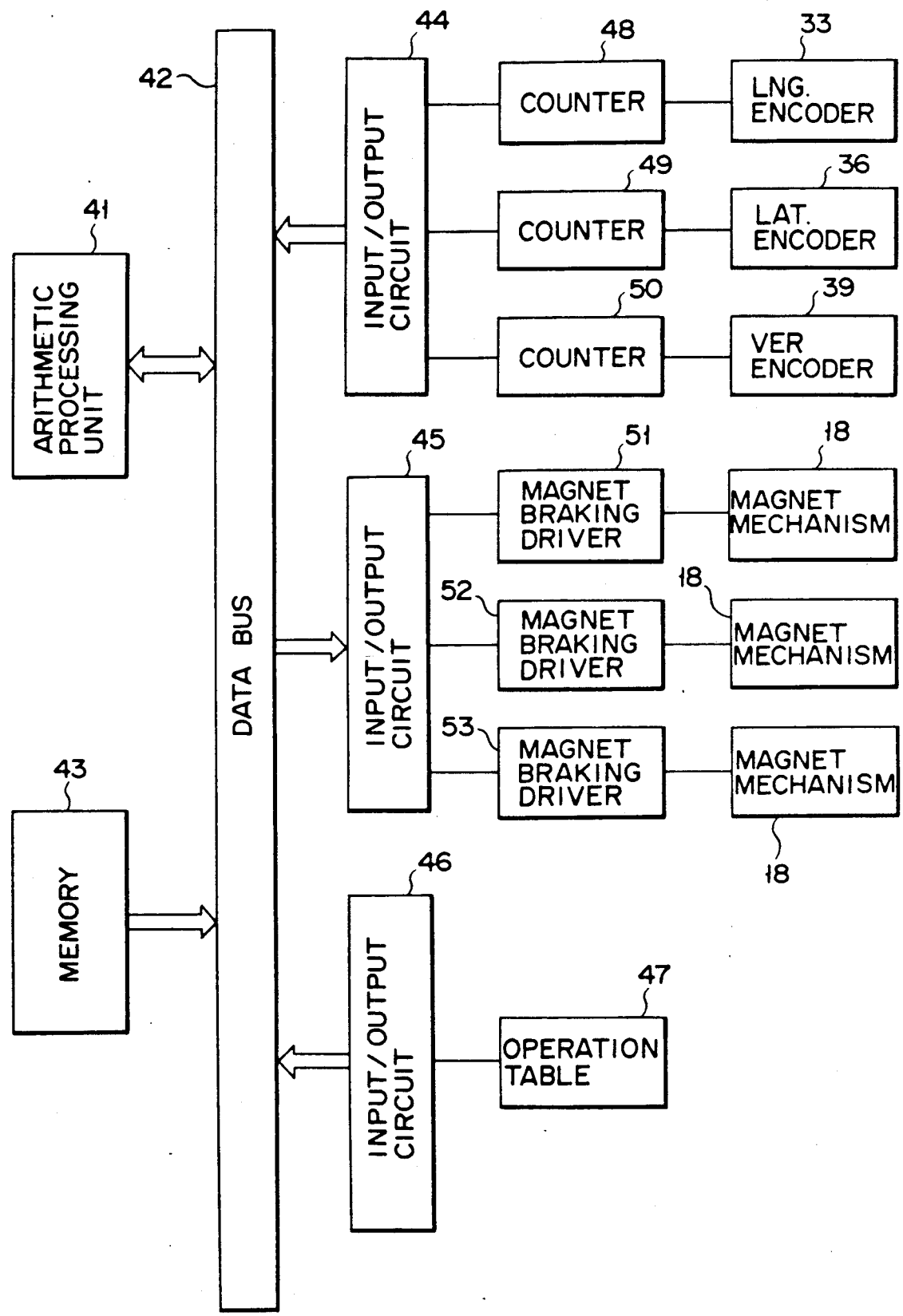
F I G. 6

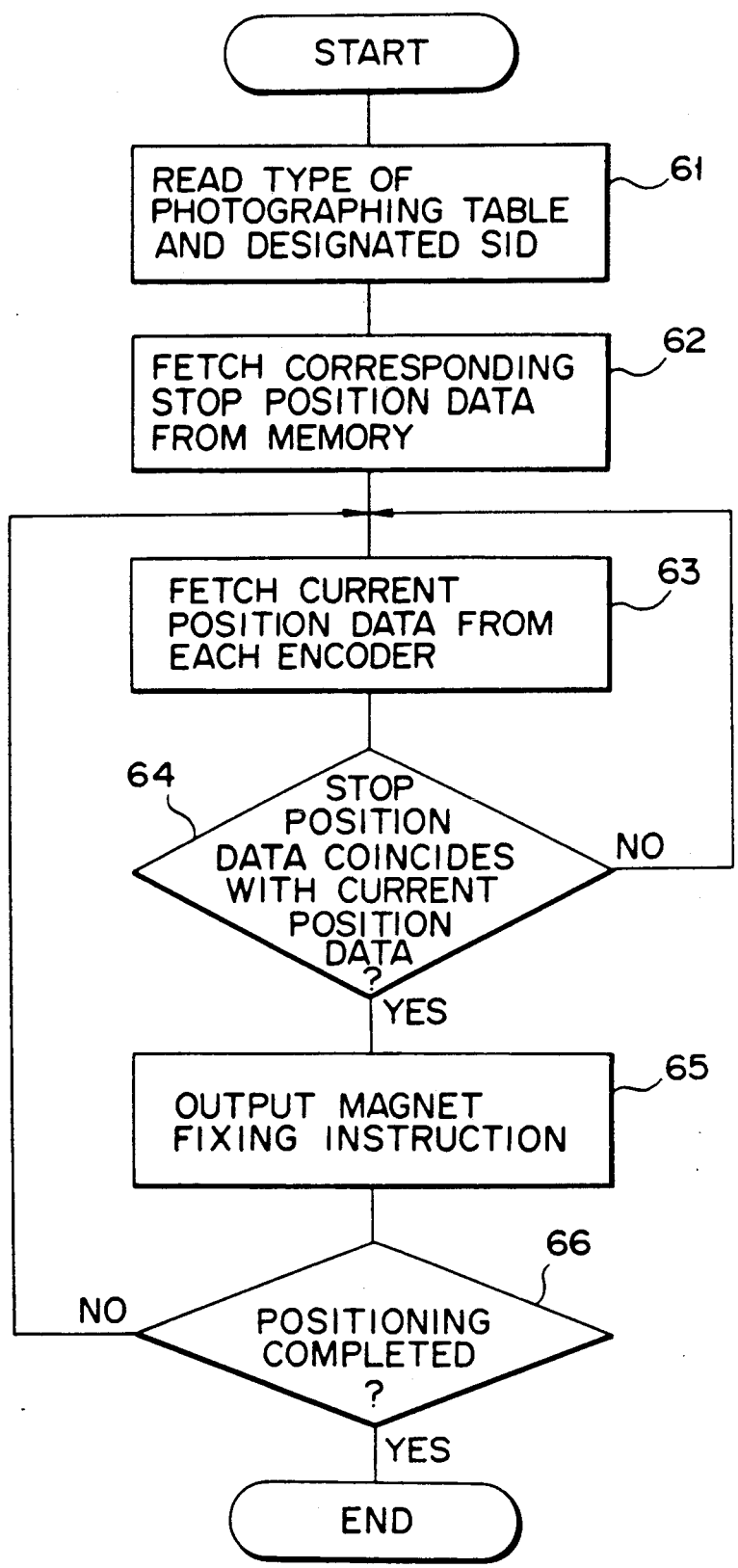
F I G. 7

X-RAY TUBE SUPPORT APPARATUS

BACKGROUND OF THE INVENTION

1. Field of the Invention

The present invention relates to a ceiling-suspended X-ray tube support apparatus.

2. Description of the Related Art

In a conventional ceiling-suspended X-ray tube support apparatus, in order to position an X-ray tube with respect to the center of, e.g., a lying or standing position photographing table, and to set a distance (to be referred to as an SID hereinafter) from a focal point of the X-ray tube to an X-ray film surface set at a predetermined position of the photographing table, a support mechanism for movably supporting the X-ray tube has been used.

This support mechanism includes a longitudinal rail mounted on a ceiling surface, and a lateral rail, disposed to be perpendicular to the longitudinal rail, and to be longitudinally movable. A proximal end portion of a vertically extendible/movable support column is supported by the lateral rail to be laterally movable. The X-ray tube is mounted at a distal end portion of the support column.

In this support mechanism, positioning of the X-ray tube with respect to the center of, e.g, the lying position photographing table is performed visually by moving the lateral rail and the support column to a central position of the photographing table. In addition, an SID is visually set at a position measured by, e.g., a measure by extending, contracting, or moving the support column. The support column and the X-ray tube are manually fixed at the central position of the photographing table and the SID set position, respectively.

Examiners, therefore, must visually position each photographing table such as a lying or standing position photographing table, thereby requiring much time and labor. In addition, a manipulation depending on vision imposes a considerable load on examiners.

SUMMARY OF THE INVENTION

It is an object of the present invention to provide a ceiling-suspended X-ray tube support apparatus for simply and easily positioning an X-ray tube with respect to the center of a photographing table, and setting an SID without depending on a vision of an examiner.

According to the present invention, there is provided an X-ray tube support apparatus comprising: an X-ray tube support mechanism for supporting an X-ray tube to be vertically extendible/movable; a guide unit, having moving paths which allow movement in two-dimensional directions parallel to a ceiling surface, for supporting the X-ray tube support mechanism, and guiding the X-ray tube to a central position of one photographing table; a plurality of position sensors, arranged in a vertical moving path of the X-ray tube support mechanism, and the two-dimensional moving paths to the central position of the photographing table, for detecting vertical and two-dimensional moving positions of the X-ray tube support mechanism; a plurality of fixing units, arranged in the two-dimensional moving paths of the guide unit and the vertical moving path of the X-ray tube support mechanism, for fixing the X-ray tube support mechanism at each moving position; and a determination unit for storing position data in accordance with the central position of the photographing table and a set distance from a focal point of the X-ray tube to an X-ray photographing system, comparing the position data with a position detection signal of the position detected by each position sensor, and outputting a lock instruction to the corresponding one of the fixing units when it is determined that the position data coincides with the position detection signal, thus locking the X-ray tube support mechanism.

When the X-ray tube support mechanism is two-dimensionally moved along moving paths of the guide unit, a position detection signal is output from the position sensor during the moving process of the X-ray tube support mechanism. This position detection signal is compared with central position data of the photographing table or SID set position data which is stored in the determination unit. When the position detection signal coincides with the central position data or the SID set position data, a lock instruction is output to the fixing unit at that position, and the X-ray support mechanism is fixed at a predetermined position in two-dimensional directions.

When the X-ray tube support mechanism is vertically moved, a position detection signal is output from the position sensor arranged along the vertical moving path of the X-ray tube support mechanism. This position detection signal is compared with SID set position data or central position data of the photographing table which is stored in the determination unit. When the position detection signal coincides with the SID set position data or the central position data, a lock instruction is output to the fixing unit, and the X-ray tube support mechanism is fixed at a predetermined position in the vertical direction.

BRIEF DESCRIPTION OF THE DRAWINGS

FIG. 6 is a block diagram of a position determination unit in the second embodiment; and FIG. 7 is a flow chart for explaining an operation of the second embodiment.

DETAILED DESCRIPTION OF THE PREFERRED EMBODIMENTS

An embodiment of the present invention will be described hereinafter with reference to the accompanying drawings.

Figure 1:
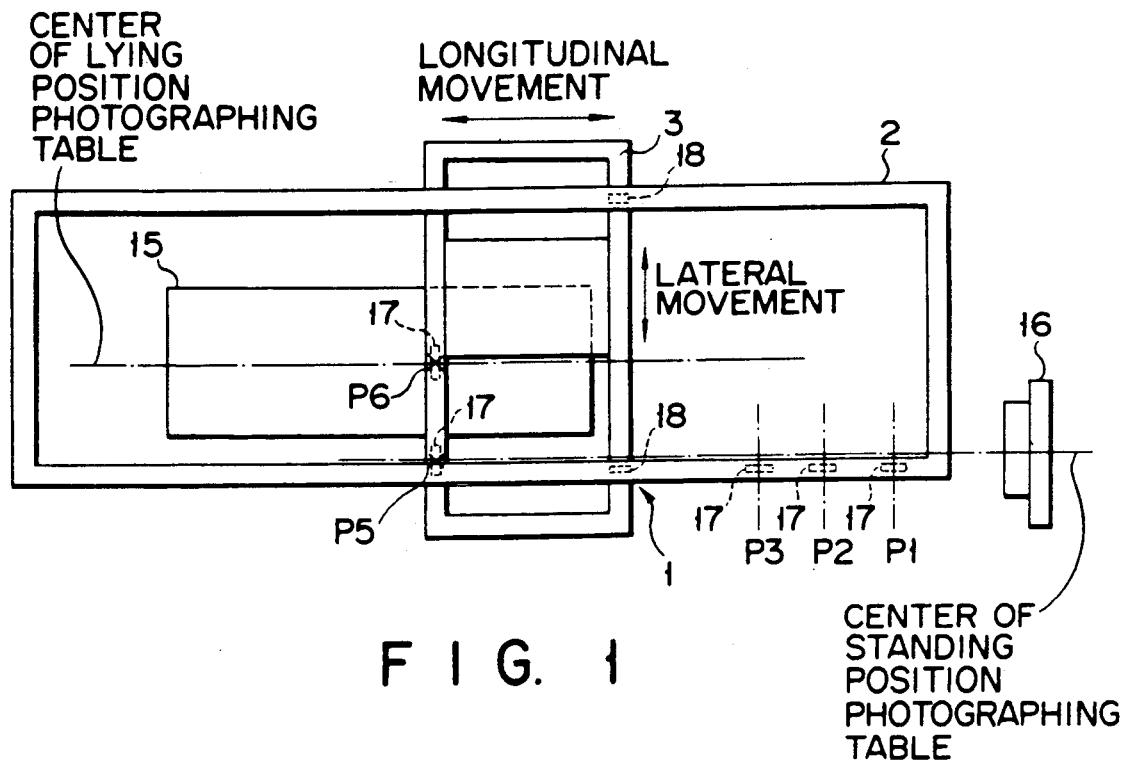
FIG. 1 is a plan view of an X-ray tube support apparatus according to the first embodiment of the present invention.
Figure 2:
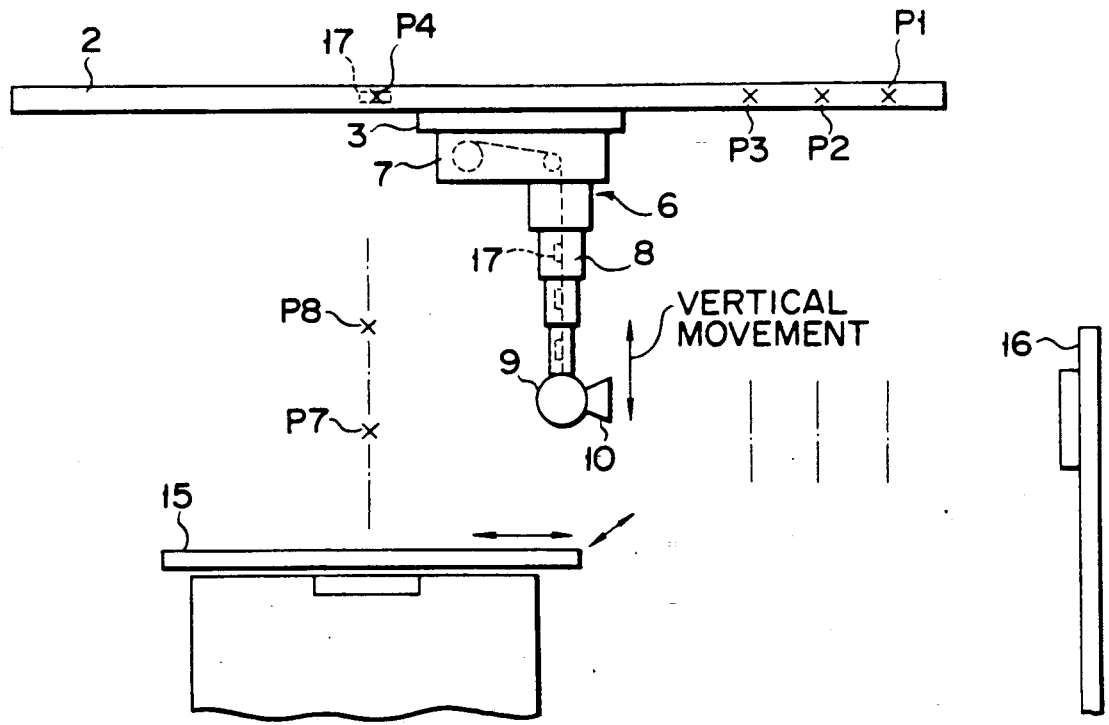
FIG. 2 is a side view of the support apparatus in the first embodiment.
Figure 3:
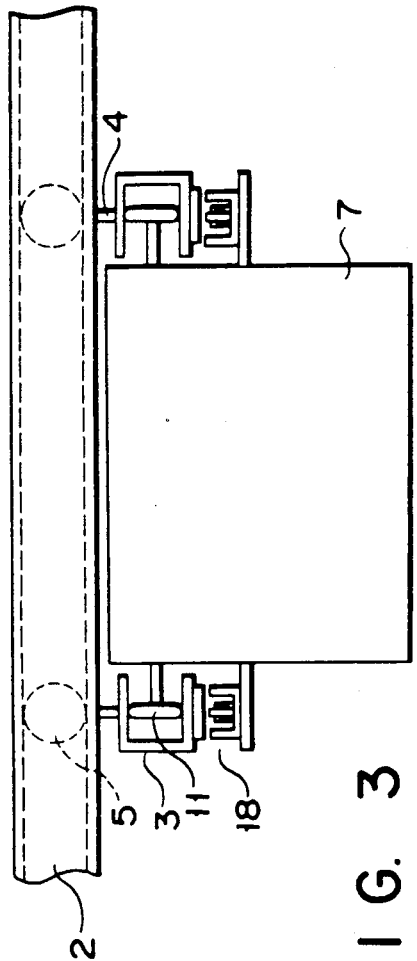
FIG. 3 is an enlarged perspective view of a part of a guide unit in the first embodiment.

As shown in FIGS. 1 and 2, a guide unit 1 is constituted by a rectangular longitudinal rail 2 mounted on a ceiling surface, and a rectangular lateral rail 3 disposed to be perpendicular to the longitudinal rail 2. As shown in FIG. 3, the longitudinal and lateral rails 2 and 3 are formed to have channel-like cross sections. The lateral rail 3 is supported by the longitudinal rail 2 to be longitudinally movable. More specifically, support legs 4 are mounted on the upper surface of the lateral rail 3 to support the lateral rail 3 on the longitudinal rail 2. Rollers 5 are axially supported by the support legs 4, respectively. The rollers 5 roll inside the channel of the longitudinal rail 2. An X-ray tube support mechanism 6 includes a support member 7, a vertically extendible/movable support column 8 held by the support member 7, and an X-ray tube 9 swingably mounted at a distal end portion of the support column 8. A stop 10 is attached to the X-ray tube 9. The X-ray tube support mechanism 6 is supported to be movable in the lateral direction of the lateral rail 3. More specifically, rollers 11 for rolling on the inner surface of the channel of the lateral rail 3 are axially supported by both side surfaces of the support member 7.

A positional relationship between the guide unit 1, the X-ray tube support mechanism 6, and a lying position photographing table 15 is as follows. The X-ray tube support mechanism 6 is set to move parallel to the lying position photographing table 15 when the lateral rail 3 is moved in the longitudinal direction of the longitudinal rail 2. The X-ray tube support mechanism 6 is also set to move parallel to the lateral direction of the lying position photographing table 15. In addition, when the support column 8 is vertically extended, contracted, or moved, the X-ray tube 9 is moved to set the SID with respect to the lying position photographing table 15.

A positional relationship between the guide unit 1, the X-ray tube support mechanism 6, and a standing position photographing table 16 is as follows. The X-ray tube support mechanism 6 is set to move in the forward-/backward direction with respect to the standing position photographing table 16 when the lateral rail 3 is moved in the longitudinal direction of the longitudinal rail 2. In other words, the SID of the X-ray tube 9 with respect to the standing position photographing table 16 can be set. The X-ray tube support mechanism 6 is also set to move parallel to the standing position photographing table 16 when the X-ray tube support mechanism 6 is moved in the lateral direction of the lateral rail 3. In addition, the X-ray tube 9 is set to move vertically with respect to the standing position photographing table 16 when the support column 8 is vertically extended, contracted, or moved.

As shown in FIGS. 1 and 2, in the ceiling-suspended X-ray tube support apparatus according to this embodiment, position identification sensors 17 are arranged at a plurality of specific longitudinal positions of the longitudinal rail 2, a plurality of specific lateral positions of the lateral rail 3, and a plurality of specific vertical positions along the moving path of the vertically extended/contracted support column 8, respectively. The position identification sensors 17 arranged at the plurality of specific longitudinal positions of the longitudinal rail 2 detect positions P1, P2, P3, and P4. The positions P1, P2, and P3 respectively correspond to distances SID-1, SID-2, and SID-3 of the X-ray tube 9 with respect to the standing photographing table 16, respectively. The position P4 corresponds to the center of the lying position photographing table 15 in the longitudinal direction. The position identification sensors 17 arranged at the plurality of specific lateral positions of the lateral rail 3 detect a position P5 corresponding to the center of the standing position photographing table 16, and a position P6 corresponding to the center of the lying position photographing table 15 in the lateral direction, respectively. The position identification sensors 17 arranged at the plurality of specific vertical positions along the moving path of the support column 8 detect positions P7 and P8 respectively corresponding to the distances SID-1 and SID-2 of the X-ray tube 9 with respect to the lying position photographing table 15.

Magnet-type fixing mechanisms 18 are mounted at the lateral rail 3, the X-ray tube support mechanism 6, and the support column 8, respectively. When a magnet of each fixing mechanism is excited, the lateral rail 3, the X-ray tube support mechanism 6, and the X-ray tube 9 are fixed to the specific longitudinal positions P1 to P4 of the longitudinal rail 2, the specific lateral position P6 of the lateral rail 3, and the specific vertical positions P7 and P8 along the moving path of the support column 8, respectively.

Figure 4:
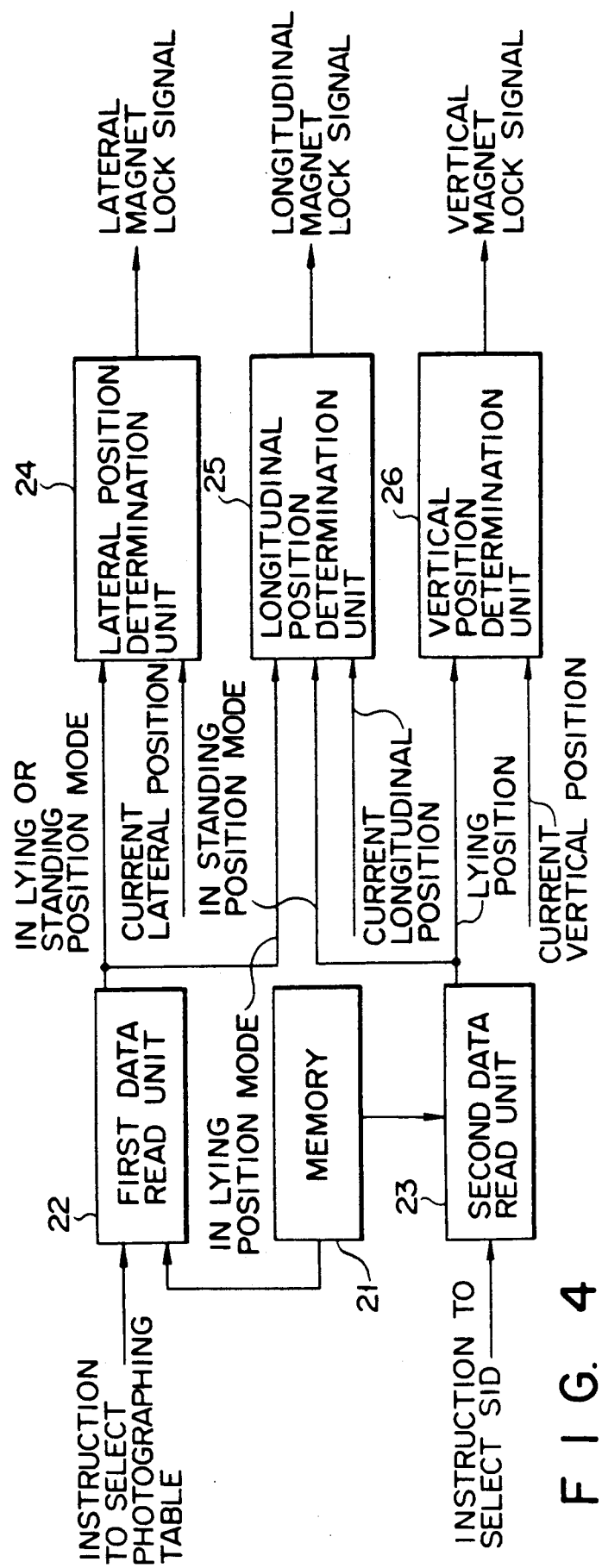
FIG. 4 is a block diagram of a position determination unit in the first embodiment.

On the other hand, as shown in FIG. 4, a positioning determination unit includes a memory 21, first and second data read units 22 and 23, a lateral position determination unit 24, a longitudinal position determination unit 25, and a vertical position determination unit 26. The memory 21 stores position data corresponding to the central positions of the lying and standing position photographing tables 15 and 16, and the SID positions. The position data consists of position data of the longitudinal, lateral, and vertical directions. When an instruction to select a photographing table is input to the first data read unit 22, the position data in the longitudinal and lateral directions and corresponding to the selected photographing table are read out from the memory 21 by the first data read unit 22. When an instruction to select the SID is input to the second data read unit 23, the position data in the longitudinal direction and the SID position data are read out from the memory 21 by the second data read unit 23. When the lying or standing position photographing table is selected, position data in the lateral direction is input from the first data read unit 22 to the lateral position determination unit 24. In addition, the position data in the lateral direction is compared with a position detection signal output from the position identification sensor arranged at the specific lateral position by the lateral position determination unit 24, and it is determined whether the position data in the lateral direction coincides with the position detection signal. If it is determined that the position detection signal coincides with the position data in the lateral direction, a lateral magnet lock instruction is supplied to the fixing mechanism in the lateral direction. When the lying position photographing table 15 is selected, longitudinal position data is input from the first data read unit 22 to the longitudinal position determination unit 25. When the standing position photographing table 16 is selected, longitudinal position data is input from the second data read unit 23 to the longitudinal position determination unit 25. The position data in the longitudinal direction is compared with the position detection signal output from the position identification sensor arranged at the specific longitudinal position by the longitudinal position determination unit 25, and it is determined whether the position data and the position detection signal in the longitudinal direction coincide with each other. If it is determined that the position detection signal and the position data in the longitudinal direction coincide with each other by the longitudinal position determination unit 25, a longitudinal magnet lock instruction is supplied to the fixing mechanism in the longitudinal direction. When the lying position photographing table is selected, SID position data is input from the second data read unit 23 to the vertical position determination unit 26. In addition, the SID position data is compared with the position detection signal output from the position identification sensor arranged at the specific vertical position along the moving path of the support column by the vertical position determination unit 26, and it is determined whether the position data and the position detection signal in the vertical direction coincide with each other. If it is determined that the position detection signal coincides with the position data in the vertical direction, a vertical magnet lock instruction is supplied to the fixing mechanism in the vertical direction.

Note that in the above embodiment, the position identification sensors 17 respectively arranged at the specific longitudinal, lateral, and vertical positions can identify the positions by assigning an identification code to each position.

When an encoder is used in place of each position identification sensor, a position can be detected as a digital value. In addition, when a potentiometer is used in place of each position identification sensor, the position can be detected as a voltage value.

An operation of this embodiment will be described hereinafter. For example, when an instruction to select the standing position photographing table 16 is supplied to the first data read unit 22, lateral position data corresponding to the central position P5 of the standing position photographing table 16 is read out from the memory 21 by the first data read unit 22. The lateral position data read out by the first data read unit 22 is supplied to the lateral position determination unit 24. In FIG. 1, first, the X-ray tube support mechanism 6 is moved along the lateral rail 3 in a direction indicated by a solid arrow. A lateral position detection signal is input to the lateral position determination unit 24 every time the X-ray support mechanism 6 reaches a position identification sensor 17 at each specific lateral position. The position detection signal in the lateral direction is compared with the lateral position data corresponding to the central position P5 by the lateral position determination unit 24, and it is determined whether the position detection signal coincides with the lateral position data. When the X-ray tube support mechanism 6 reaches the central position P5, a coincidence of the position detection signal of the position detected by the position identification sensor 17 and the lateral position data corresponding to the central position P5 is determined by the lateral position determination unit 24. A lateral magnet lock instruction is output from the lateral position determination unit 24 to the fixing mechanism in the lateral direction. As a result, the X-ray tube support mechanism 6 is fixed at the central position P5 of the standing position photographing table 16.

An instruction to select the position P1 as the SID position of the standing position photographing table 16 is supplied to the second data read unit 23. Then, the position data of the standing position photographing table 16 in the longitudinal direction and corresponding to the SID position P1 is read out from the memory 21 to the second data read unit 23. The position data read out by the second data read unit 23 is supplied to the longitudinal position determination unit 25. In FIG. 1, the lateral rail 3 is moved along the longitudinal rail 2 in a direction indicated by a solid arrow. At this time, a position detection signal in the longitudinal direction is input to the longitudinal position determination unit 25 every time the lateral rail 3 reaches a position identification sensor 17 at each specific longitudinal position. The position detection signal in the longitudinal direction is compared with the SID position data corresponding to the SID position P1 by the longitudinal position determination unit 25, and it is determined whether the position detection signal coincides with the SID position data. When the lateral rail 3 reaches the SID position P1 of the standing position photographing table 16, a coincidence of the position detection signal of the position detected by the position identification sensor 17 in the longitudinal direction and the SID position data corresponding to the SID position P1 is determined by the longitudinal position determination unit 25. A longitudinal magnet lock instruction is output from the longitudinal position determination unit 25 to the fixing mechanism in the longitudinal direction. As a result, the lateral rail 3 is fixed at the SID position P1 of the standing position photographing table 16.

The above description is made with reference to a case wherein the SID position P1 of the standing position photographing table 16 is selected. When the SID position P2 or P3 is selected, the lateral rail 3 is fixed to the SID position P2 or P3, following the same operation as in the above description.

A case wherein positioning with respect to the lying position photographing table 15 and the SID positioning are performed will be described below. An instruction to select the lying position photographing table 15 is supplied to the first data read unit 22. Then, longitudinal and lateral position data respectively corresponding to the central positions P4 and P6 of the lying position photographing table 15 in the longitudinal and lateral directions are read out from the memory 21 by the first data read unit 22. The lateral position data read out by the first data read unit 22 is input to the lateral position determination unit 24, and the longitudinal position data is input to the longitudinal position determination unit 25. In FIG. 1, first, the lateral rail 3 is moved along the longitudinal rail 2 in a direction indicated by a solid arrow. A position detection signal in the longitudinal direction is input to the longitudinal position determination unit 25 every time the lateral rail 3 reaches a position identification sensor 17 at each specific longitudinal position. The position detection signal of the position detected by the position identification sensor 17 in the longitudinal direction is compared with the longitudinal position data corresponding to the central position P4 by the longitudinal position determination unit 25, and it is determined whether the position detection signal coincides with the longitudinal position data. When the lateral rail 3 reaches the central position P4 of the lying position photographing table 15, a coincidence of the position detection signal of the position detected by the position identification sensor 17 at the specific longitudinal position and the longitudinal position data is determined by the longitudinal position determination unit 25. A longitudinal magnet lock instruction is output from the longitudinal position determination unit 25 to the fixing mechanism in the longitudinal direction. Therefore, the lateral rail 3 is fixed at the central position P4 of the lying position photographing table 15 in the longitudinal direction. Then, the X-ray tube support mechanism 6 is moved along the lateral rail 3 in a direction indicated by a solid arrow in FIG. 1. A lateral position detection signal is input to the lateral position determination unit 24 every time the X-ray tube support mechanism 6 reaches a position identification sensor 17 at each specific lateral position. The position detection signal of the position detected by the position identification sensor 17 in the lateral direction is compared with the lateral position data corresponding to the central position P6 of the lying position photographing table 15 in the lateral direction, and it is determined whether the position detection signal coincides with the lateral position data. When the X-ray tube support mechanism 6 reaches the central position P6 in the lateral direction, a coincidence of the position detection signal of the position detected by the position identification sensor 17 at the specific lateral position and the lateral position data is determined by the lateral position determination unit 24, and a lateral magnet lock instruction is output from the lateral position determination unit 24 to the fixing mechanism in the lateral direction. As a result, the X-ray tube support mechanism 6 is fixed at the central position P5 of the lying position photographing table 15 in the lateral direction.

On the other hand, an instruction to select the position P7 as the SID position with respect to the support column 8 in the vertical direction is supplied to the second data read unit 23. Then, position data corresponding to the SID position P7 of the support column 8 is read out from the memory 21 by the second data read unit 23. The position data read out by the second data read unit 23 is supplied to the vertical position determination unit 26. In FIG. 1, the support column 8 of the support mechanism 6 is vertically moved, as indicated by a solid arrow. A vertical position detection signal is input to the vertical position determination unit 26 every time the X-ray tube 9 reaches a position identification sensor 17 at each specific vertical position along the moving path of the support column 8. The position detection signal of the position detected by the vertical position identification sensor 17 is compared with SID position data corresponding to the SID position P7 by the vertical position determination unit 26, and it is determined whether the position detection signal coincides with the SID position data. When the support column 8 reaches the SID position P7 of the lying position photographing table 15, a coincidence of the position detection signal of the position detected by the vertical position identification sensor 17 and the SID position data corresponding to the SID position P7 is determined by the vertical position determination unit 26. A vertical magnet lock instruction is output from the vertical position determination unit 26 to the fixing mechanism in the vertical direction. As a result, the support column 8 is fixed at the SID position P7 of the lying position photographing table 15.

The above description is made with reference to a case wherein the SID position P7 of the lying position photographing table 15 is selected. When the SID position P8 is selected, the support column 8 can be fixed at the SID position P8 following the same operation as in the above description.

Another embodiment of the present invention will be described hereinafter with reference to FIGS. 5 to 7.

Figure 5:
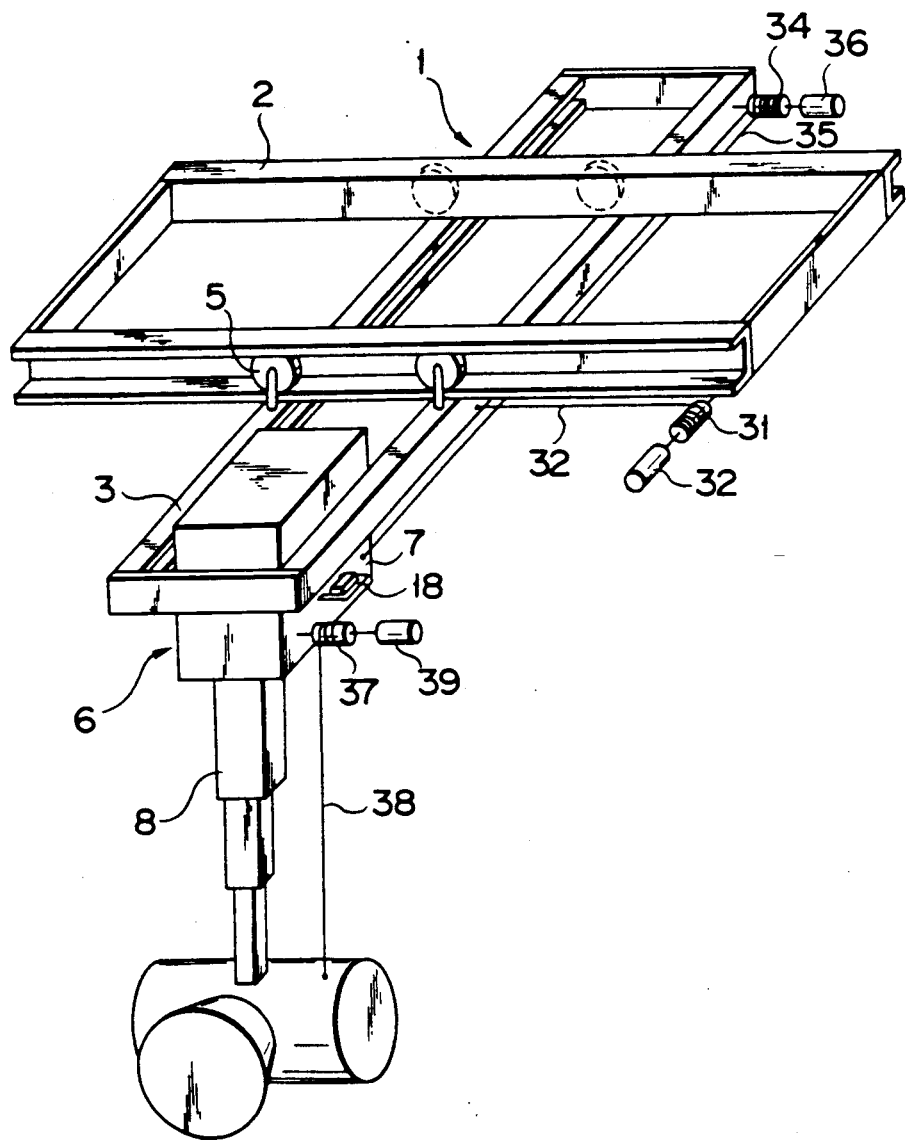
FIG. 5 is a perspective view of an X-ray tube support apparatus according to the second embodiment of the present invention.

In FIG. 5, a guide unit 1 and a support mechanism 6 are the same as those in the arrangement in FIGS. 1 and 2. Therefore, the same reference numerals in FIG. 5 denote the same parts as in FIGS. 1 and 2, and a description thereof will be omitted. A take-up drum 31 is rotatably mounted on a side surface at one end portion in the longitudinal direction of a longitudinal rail 2. A wire 32 taken up or rewound by the take-up drum 31 is coupled to a lateral rail 3. A longitudinal-direction encoder 33 is mounted on a rotating shaft of the take-up drum 31. The take-up drum 31 is set to rotate upon longitudinal movement of the lateral rail 3. A rotation of the take-up drum 31 is converted into a pulse signal in accordance with a moving amount of the lateral rail 3. A take-up drum 34 is rotatably mounted on a side surface of one end portion in the lateral direction of the lateral rail 3. A wire 35 taken up or rewound by the take-up drum 34 is coupled to a support member 7 of the X-ray tube support mechanism 6. A lateral-direction encoder 36 is mounted at a rotational shaft of the take-up drum 34. The take-up drum 34 is set to rotate upon lateral movement of the X-ray tube support mechanism 6. A rotation of the take-up drum 34 is converted into a pulse signal in accordance with a moving amount of the X-ray tube support mechanism 6. In addition, a take-up drum 37 is rotatably mounted on one side surface of the support member 7 of the X-ray tube support mechanism 6. A wire 38 taken up or rewound by the take-up drum 37 is coupled to a proper position of the X-ray tube. A vertical-direction encoder 39 is mounted on a rotating shaft of the take-up drum 37. The take-up drum 37 is set to rotate upon vertical movement of the X-ray tube support column 8. A rotation of the take-up drum 37 is converted into a pulse signal in accordance with a vertical moving amount of the X-ray tube support column 8.

As shown in FIG. 6, an arithmetic processing unit 41 is connected to a memory 43, and input/output (I/O) circuits 44, 45, and 46 through a data bus 42. The memory 43 stores longitudinal, lateral, and vertical position data corresponding to a plurality of different photographing tables, and a plurality of SIDs. When the type of the photographing table and the SID are designated by an operation table 47, these designation data are fetched in the arithmetic processing unit 41 through the I/O circuit 46 and the data bus 42. A pulse signal output from the longitudinal-direction encoder 33 is counted by a counter 48. A pulse signal output from the lateral-direction encoder 36 is counted by a counter 49. A pulse signal output from the vertical-direction encoder 39 is counted by a counter 50. The count values of the counters 48 to 50 are fetched in the arithmetic processing unit 41 through the I/O circuit 44 and the bus 42. This arithmetic processing unit 41 has a determination function for respectively comparing the longitudinal, lateral, and vertical position data read out from the memory 43 with the count values fetched from the counters 48 to 50 to determine whether they coincide with each other, and a function for outputting a magnet fixing instruction to magnet braking drivers 51 to 53 through the data bus 42 and the I/O circuit 45 when it is determined that each position data coincides with the corresponding count value by the determination function.

An operation of the position determination unit having the above arrangement will be described below with reference to a flow chart in FIG. 7. In step 61, data of a type of the photographing table and the SID which are designated by the operation table 47 are read by the arithmetic processing unit 41 through the I/O circuit 46. In step 62, longitudinal, lateral, and vertical data corresponding to the designated data are read out from the memory 43 to the arithmetic processing unit 41 as stopping coordinate data. When the lateral rail 3 is moved along the longitudinal rail 2, a pulse signal corresponding to a moving amount of the lateral rail 3 output from the longitudinal-direction encoder 33 is counted by the counter 48, as described above. In step 63, the count value of the counter 48 is read by the arithmetic processing unit 41 through the I/O circuit 44 as current position data. In step 64, the stopping coordinate data in the longitudinal direction is compared with the current value, and it is determined whether they coincide with each other. If the stopping coordinate data does not coincide with the current value, the flow returns to step 63, and a reading operation of the current position data in the longitudinal direction is continued. If it is determined that the stopping coordinate data coincides with the current value in step 64, a magnet fixing instruction is supplied to the magnet braking driver 51 in the longitudinal direction through the I/O circuit 45 in step 65.

The above description is made with reference to longitudinal movement. However, the same processing as in the above description is performed when the X-ray tube support mechanism 6 is moved along the lateral rail 3, or when the support column 8 of the X-ray tube support mechanism 6 is vertically moved, and hence a description thereof will be omitted.

If it is determined that positioning in all the longitudinal, lateral, and vertical directions is completed in step 66, a series of operations with respect to the designation data are completed. If the positioning in all the directions is not completed, the flow returns to step 63.

As described above, according to the present invention, a position detection signal of the X-ray tube support mechanism which two-dimensionally moves along moving paths of the guide unit, and a position detection signal of the X-ray tube support mechanism which vertically moves are compared with position data corresponding to designation data of the photographing table and the SID. If each position detection signal coincides with the corresponding position data, a lock instruction is output tot he fixing unit of the corresponding position to fix the X-ray tube support mechanism in position, and hence the X-ray tube support mechanism need only be moved to the position at which the mechanism is fixed. Therefore, positioning can be easily performed and a time period required for positioning can be shortened, thereby reducing a load imposed on examiners.

What is claimed is:

1. An X-ray tube support apparatus comprising:
   X-ray tube supporting means for supporting an X-ray tube to be vertically extendible;
   guiding means, having moving paths which allow movement in two-dimensional directions parallel to a ceiling surface, for supporting said X-ray tube supporting means, and guiding said X-ray tube to a central position of one horizontally movable photographing table;
   a plurality of position detecting means, arranged in a vertical moving path of said X-ray tube supporting means, and the two-dimensional moving paths to the central position of said photographing table, for detecting current positions of said X-ray tube supporting means in accordance with vertical and two-dimensional movements thereof;
   a plurality of fixing means, arranged in the two-dimensional moving paths of said guiding means and the vertical moving path of said X-ray tube supporting means, for fixing the position of said X-ray tube supporting means; and
   determining means for storing position data corresponding to the central position of said photographing table and a set distance from a focal point of said X-ray tube to an X-ray photographing system, comparing the position data with a position detecting signal of the position detected by said each position detection means, and outputting a lock instruction to the corresponding one of said fixing means when it is determined that the position data coincides with the position detection signal, thus locking said X-ray tube supporting means.

2. An apparatus according to claim 1, wherein said one photographing table includes a lying position photographing table.

3. An apparatus according to claim 1, wherein said one photographing table includes a standing position photographing table.

4. An apparatus according to claim 1, wherein said X-ray tube supporting means comprise an X-ray tube support mechanism including a support member, a vertically extendible/movable support column held by said support member, and an X-ray tube mounted at a distal end of said support column.

5. An apparatus according to claim 1, wherein said guiding means includes a longitudinal rail, and a lateral rail, mounted to be movable in a longitudinal direction of said longitudinal rail, for supporting said X-ray tube supporting means to be movable in a lateral direction.

6. An apparatus according to claim 1, wherein each of said position detection means includes an encoder.

7. An apparatus according to claim 1, wherein each of said position detection means includes a potentiometer.

8. An apparatus according to claim 1, wherein each of said position detection means includes a position identification sensor.

9. An apparatus according to claim 1, wherein each of said fixing means includes an electromagnet.

10. An X-ray tube support apparatus comprising:
    X-ray tube supporting means for supporting an X-ray tube to be vertically extendible;
    guiding means, having moving paths which allow movement in two-dimensional directions parallel to a ceiling surface, for supporting said X-ray tube supporting means, and guiding said X-ray tube to a central position of one of a plurality of difference photographing tables including lying and standing position photographing tables;
    a plurality of position detecting means, arranged in a vertical moving path of said X-ray tube supporting means, and the two-dimensional moving paths to the central position of each of said photographing tables, for detecting positions of said X-ray tube supporting means in accordance with vertical and two-dimensional movements thereof;
    fixing means, arranged in the moving paths of said guiding means corresponding to the central position of said each of said X-ray tube supporting means, for selectively fixing the position of said X-ray tube supporting means;
    memory means for storing position data corresponding to the central position of said each of said photographing tables, and a distance from said X-ray tube to an X-ray photographing system; and
    determining means for comparing the position data stored in said memory means with a position detection signal of the position detected by said position detection means, and outputting a lock instruction to said fixing means when it is determined that the position data coincides with the position detection signal.

11. An apparatus according to claim 10, wherein said determining means comprises a data read unit for reading the corresponding position data from said memory means when instructions to select a type of said photographing tables and a distance from said X-ray tube to said X-ray photographing system are input, and a position determining unit for comparing the position data read out by said data read unit with the position detection signal of the position detected by each of said position detection means serving as a current position signal to determine whether the data and the signal coincide with each other.

* * * * *